United States Patent
Bengali et al.

(10) Patent No.: US 10,850,275 B2
(45) Date of Patent: Dec. 1, 2020

(54) GOLD SENSOR

(71) Applicant: HEWLETT-PACKARD DEVELOPMENT COMPANY, L.P., Houston, TX (US)

(72) Inventors: Sadiq Bengali, Corvallis, OR (US); Manish Giri, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 208 days.

(21) Appl. No.: 15/749,036

(22) PCT Filed: Jan. 29, 2016

(86) PCT No.: PCT/US2016/015550
§ 371 (c)(1),
(2) Date: Jan. 30, 2018

(87) PCT Pub. No.: WO2017/131726
PCT Pub. Date: Aug. 3, 2017

(65) Prior Publication Data
US 2018/0229236 A1  Aug. 16, 2018

(51) Int. Cl.
*B01L 3/00* (2006.01)
*G01N 33/553* (2006.01)

(52) U.S. Cl.
CPC ........... *B01L 3/502707* (2013.01); *B01L 3/00* (2013.01); *G01N 33/553* (2013.01); *B01L 2300/0663* (2013.01); *B01L 2300/1827* (2013.01); *B01L 2400/0442* (2013.01)

(58) Field of Classification Search
CPC ............... B01L 3/502707; B01L 3/00; B01L 2400/0442; B01L 2300/1827; B01L 2300/0663; G01N 33/553
See application file for complete search history.

(56) References Cited

U.S. PATENT DOCUMENTS

| | | | |
|---|---|---|---|
| 6,169,394 | B1 | 1/2001 | Frazier et al. |
| 6,889,567 | B2 | 5/2005 | Cabuz |
| 2004/0099531 | A1 | 5/2004 | Srinivasan et al. |
| 2004/0147032 | A1 | 7/2004 | Martin et al. |

(Continued)

FOREIGN PATENT DOCUMENTS

| | | |
|---|---|---|
| CN | 101650370 | 2/2010 |
| CN | 101687191 A | 3/2010 |

(Continued)

OTHER PUBLICATIONS

MiniMed 530g, 2015 Medtronic MiniMed, Inc, URL: http://www.medtronicdiabetes.com/products/minimed-530g-diabetes-system-with-enlite International Searching Authority, International Search Report and Written Opinion for PCT Application No. PCT/US2016/015550, dated Oct. 27, 2016, 10 pages.

*Primary Examiner* — Benjamin R Whatley
*Assistant Examiner* — Jean Caraballo-Leon
(74) *Attorney, Agent, or Firm* — Fabian VanCott

(57) ABSTRACT

A microfluidic diagnostic chip may, in an example, include a number of microfluidic channels defined in a substrate each microfluidic channel fluidly coupled to at least one fluidic slot; the at least one fluidic slot to receive a number of fluids, and a number of gold sensors each gold sensor having a thickness of between 1500 and 5000 angstroms (Å).

9 Claims, 8 Drawing Sheets

(56) References Cited

U.S. PATENT DOCUMENTS

| | | | |
|---|---|---|---|
| 2004/0179427 A1* | 9/2004 | Yamazaki | B01F 13/02 366/348 |
| 2005/0175505 A1 | 8/2005 | Cantor et al. | |
| 2007/0153284 A1* | 7/2007 | Glazier | B82Y 15/00 356/445 |
| 2011/0027128 A1 | 2/2011 | Gridelet | |
| 2012/0058504 A1* | 3/2012 | Li | B01L 3/502761 435/29 |
| 2013/0293878 A1* | 11/2013 | Chang | G01N 21/6454 356/213 |
| 2014/0042017 A1 | 2/2014 | Harttig | |
| 2014/0072962 A1* | 3/2014 | Kelley | C12Q 1/701 435/5 |
| 2014/0125359 A1* | 5/2014 | El-Gamal | G01N 27/223 324/664 |
| 2015/0346104 A1* | 12/2015 | Chou | G01N 21/763 436/501 |

FOREIGN PATENT DOCUMENTS

| | | |
|---|---|---|
| EP | 1362827 | 11/2003 |
| JP | 2014205056 | 10/2014 |
| WO | WO-9712063 | 4/1997 |
| WO | WO-2014055559 | 4/2014 |
| WO | WO-2014210388 | 12/2014 |
| WO | WO-2015084800 | 6/2015 |

* cited by examiner

GOLD SENSOR

BACKGROUND

Infectious diseases and other medical conditions affect human life on a continual basis. Developments have been made to detect the presence of an analyte such as antigens in blood or other bodily fluids in order to diagnose a patient's illness or prevent illnesses from occurring. In some cases, a device is used to analyze such an analyte.

BRIEF DESCRIPTION OF THE DRAWINGS

The accompanying drawings illustrate various examples of the principles described herein and are a part of the specification. The illustrated examples are given merely for illustration, and do not limit the scope of the claims.

Throughout the drawings, identical reference numbers designate similar, but not necessarily identical, elements.

DETAILED DESCRIPTION

Figure 1:
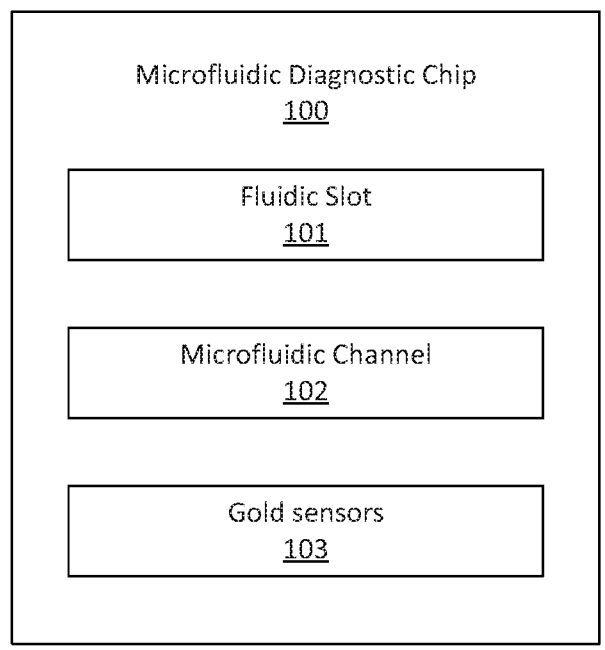
FIG. 1 is a block diagram of a microfluidic diagnostic chip according to an example of the principles described herein.

As mentioned above, certain devices may be used to analyze an analyte within a fluid. One of these devices, a microelectromechanical system (MEMS) device included within a microfluidic diagnostic chip, may be used to help detect pathogens in the human body, for example, and diagnose an illness in a patient. A microfluidic diagnostic chip (MDC) may receive a fluid including an analyte in a fluidic slot on the MDC and analyze it for purposes of attempting to diagnose a disease in a sample from a subject or some other sample of interest.

A number of channels may be defined in a substrate of the microfluidic chip in order to allow the analyte to be pumped there through with a number of pumps. A number of sensors may be used to conduct a number of diagnostics on the analyte. These sensors may detect changes in an electric field created by the sensors as portions of the analyte such as blood cells in a blood sample pass over the sensor. However, as the microfluidic chips get smaller and the voltages used to drive the sensors get lower, any disturbance in the electromagnetic field may distort the sensor readings causing false positive results and/or inconclusive results.

The present specification, therefore describes a microfluidic diagnostic chip that, in an example, includes a number of microfluidic channels defined in a substrate each microfluidic channel fluidly coupled to at least one fluidic slot; the at least one fluidic slot to receive a number of fluids, and a number of gold sensors each gold sensor having a thickness of between 1500 and 5000 angstroms (Å).

The present specification further describes a method of forming a microfluidic diagnostic chip that, in an example, includes forming a layer of tantalum over a portion of a substrate, forming a layer of gold over a portion of the layer of tantalum to form a number of gold sensors, and forming a layer of silicone carbide over any portion of tantalum exposed after the formation of the layer of gold.

The present specification also describes a microelectromechanical system (MEMS) that, in one example, includes a fluidic feed slot into which an amount of an analyte is to be introduced, a number of fluidic channels fluidly coupled to the fluidic slot, a number of gold sensors formed on top of a layer of tantalum, and a passivation layer formed over the tantalum.

As used in the present specification and in the appended claims, the term "portion" is meant to be understood as an amount, section, or piece of something not totaling the whole amount, section, or piece.

Further, as used in the present specification and in the appended claims, the term "analyte" is meant to be understood as any substance within a fluid that may be placed in a microelectromechanical system (MEMS) device such as a microfluidic diagnostic chip (MDC). In one example, the analyte may be any constituent substance within a fluid such as, but not limited to, animal or human blood, animal or human urine, animal or human feces, animal or human mucus, animal or human saliva, yeast, or antigens, among others.

Even still further, as used in the present specification and in the appended claims, the term "a number of" or similar language is meant to be understood broadly as any positive number comprising 1 to infinity.

In the following description, for purposes of explanation, numerous specific details are set forth in order to provide a thorough understanding of the present systems and methods. It will be apparent, however, to one skilled in the art that the present apparatus, systems and methods may be practiced without these specific details. Reference in the specification to "an example" or similar language means that a particular feature, structure, or characteristic described in connection with that example is included as described, but may not be included in other examples.

FIG. 1 is a block diagram of a microfluidic diagnostic chip (100) according to one example of the principles described herein. The microfluidic diagnostic chip (100) may include a number of small microelectromechanical system (MEMS) devices. The microfluidic diagnostic chip (100) includes at least one fluidic slot (101) into which an analyte may be introduced. The fluidic slot (101) may be fluidically coupled to a number of microfluidic channels (102). The number of microfluidic channels (102) may direct the analyte across a number of sensors such as plurality of gold sensors (103).

In an example, the number of gold sensors (103) is two: a first gold sensor (103) acting as an electrode and a second gold sensor (103) acting as ground. In an example, fluids associated with the analyte may be used to close the circuit between the first gold sensor (103) and the second gold sensor (103). Once the circuit between the first gold sensor (103) and the second gold sensor (103), an electric field may be created. As the analyte continues to pass over the two sensors (103) changes in the electric field due to a presence of different types of conductive or non-conductive constituents of the analyte may be detected by the two sensors.

As will be described in more detail below, in an example, the gold sensors (103) may be deposited on to the top of a tantalum layer with the tantalum layer being placed intermediate to a substrate surface, such as a dielectric material, and the gold sensors (103). In an example, this layer of tantalum may have a thickness of approximately 2000 Å (±1000 Å). In an example, the layer of tantalum may have a thickness of between approximately 1000 A to 3000 A. Tantalum is a relatively highly electrically conductive metal that, in itself, creates an electric field. In addition to the electric field created by the gold sensors (103), the electric field created by the layer of tantalum may distort sensor readings and cause a misdiagnosis if such a microfluidic diagnostic chip (100) is used. To reduce or eliminate this additional electric field created by the layer of tantalum, a layer of silicon carbide (SiC) may cover the layer of tantalum. In an example, the thickness of the passivation layer is 1500 Å (±500 Å). In an example, the thickness of the passivation layer is between approximately 1000 Å to 2000 Å. The presence and thickness of the passivation layer reduces or even eliminates entirely the electric field created by the tantalum under the gold sensors (103).

As will be descried in more detail below, the gold sensors (103) may include a binding surface to which a biomarker such as an antibody may be bound. This functionalized binding surface may be used to react in some way with the analyte in order to further diagnose an illness or identify an analyte (i.e., biomarker) within the fluid. The identification of the analyte (e.g. biomarker) occurs when the analyte binds to, for example, an antibody on the binding surface.

The thickness of the gold sensors (103) may, in an example, be between 1500 Å to 3500 Å. In an example, the thickness of the gold sensors (103) may be 2500 Å. The thickness of the gold sensors (103) may be such that rough edges are not produced by the layer of gold. Where the thickness of the gold sensors (103) is increased beyond, for example, 3500 Å, a number of rough edges may be created distorting the electric field produced by the gold sensors (103). This may also result in poor sensor readings and eventual misdiagnosis or analysis of the analyte.

Figure 2:
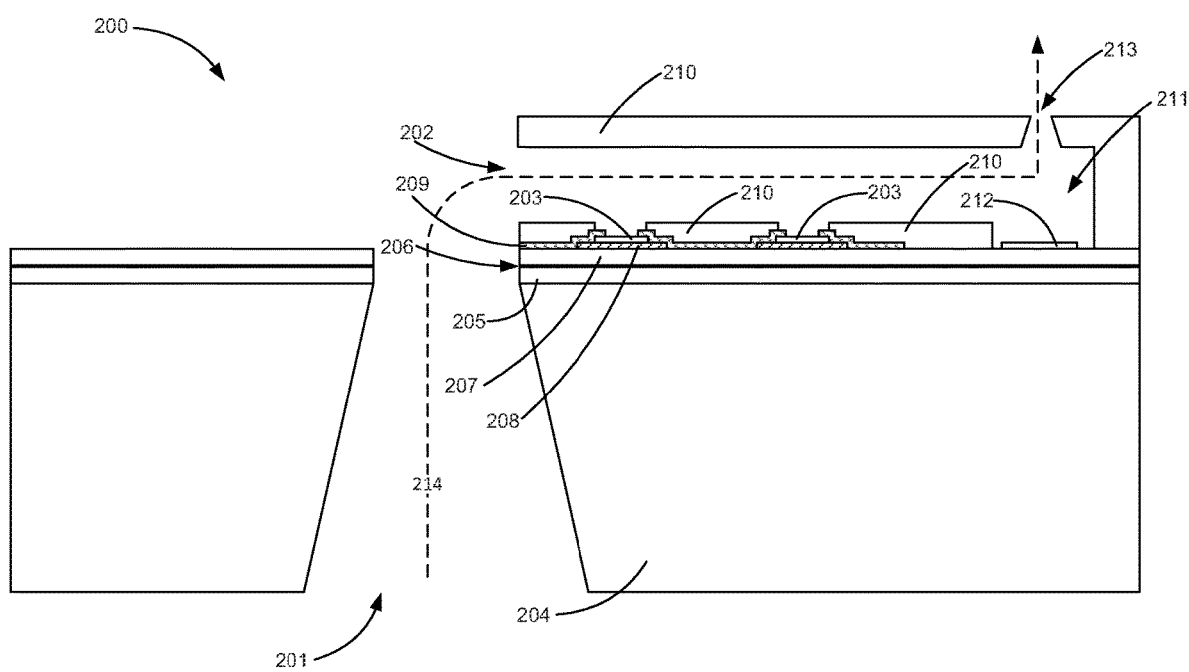
FIG. 2 is a side cut out view of a microfluidic diagnostic chip according to an example of the principles described herein.
Figure 3A:
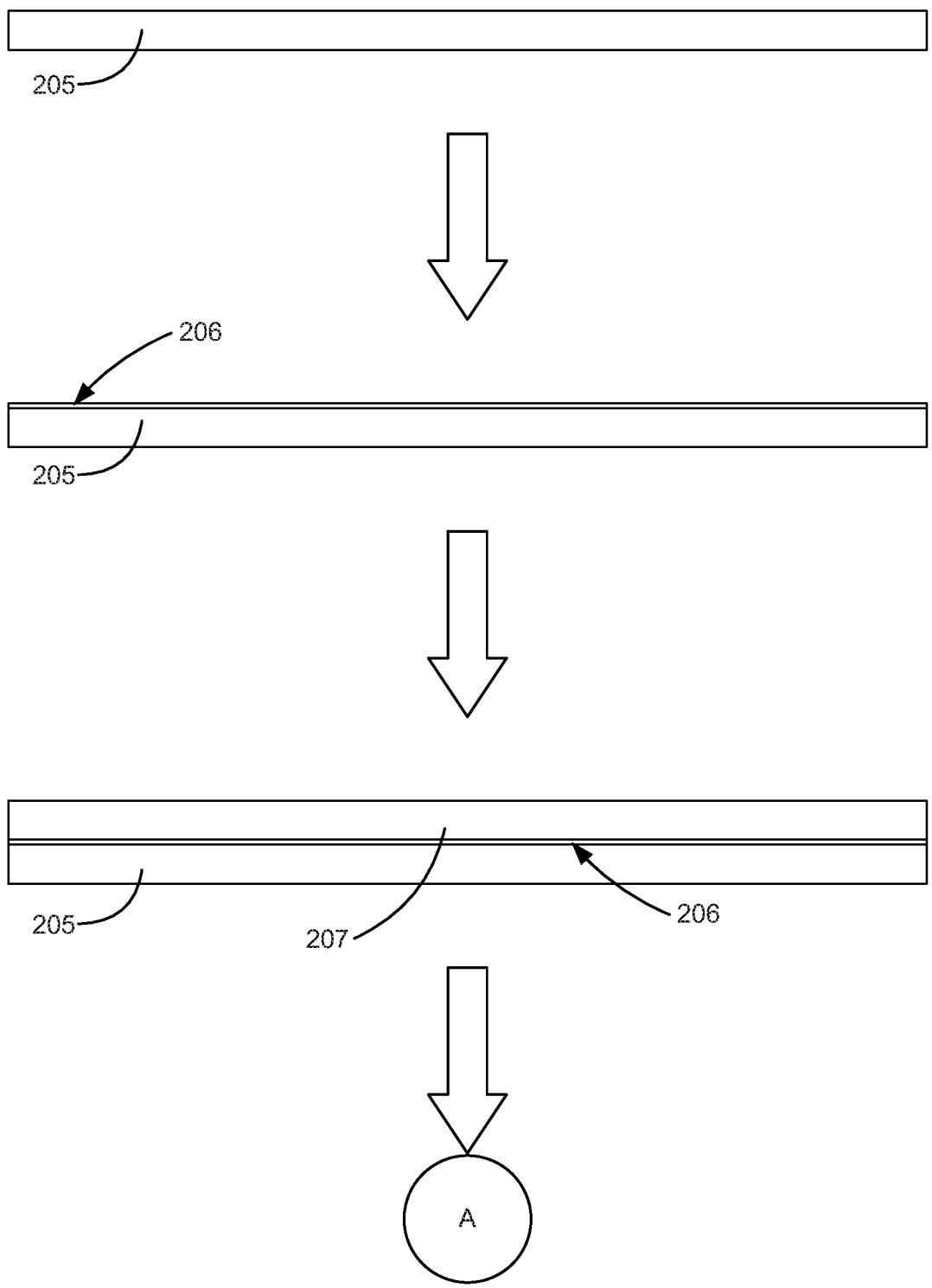
FIGS. 3A through 3C is a sequence of block diagrams showing a formation process of the microfluidic diagnostic chip of FIG. 2 according to an example of the principles described herein.
Figure 3B:
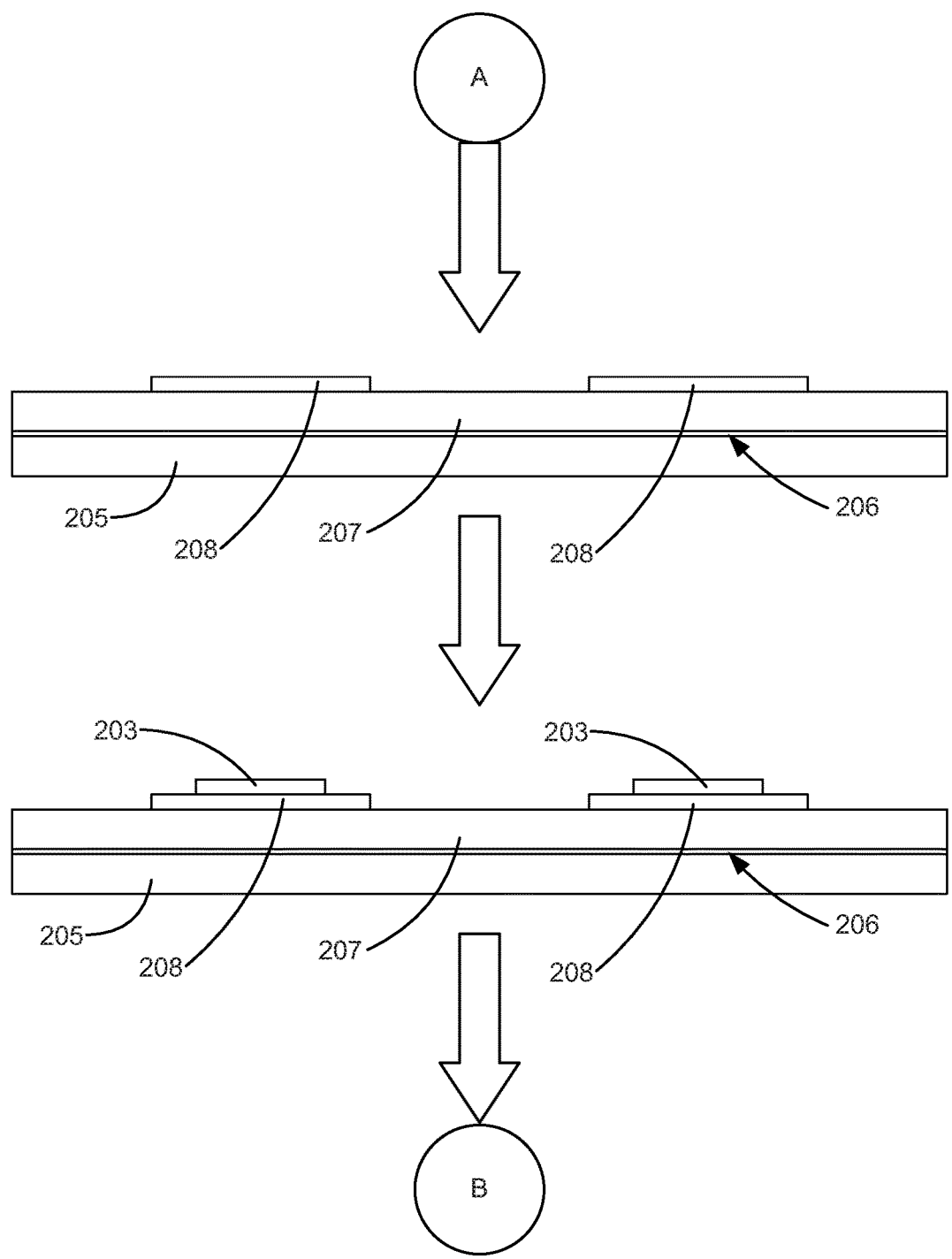
Figure 3C:
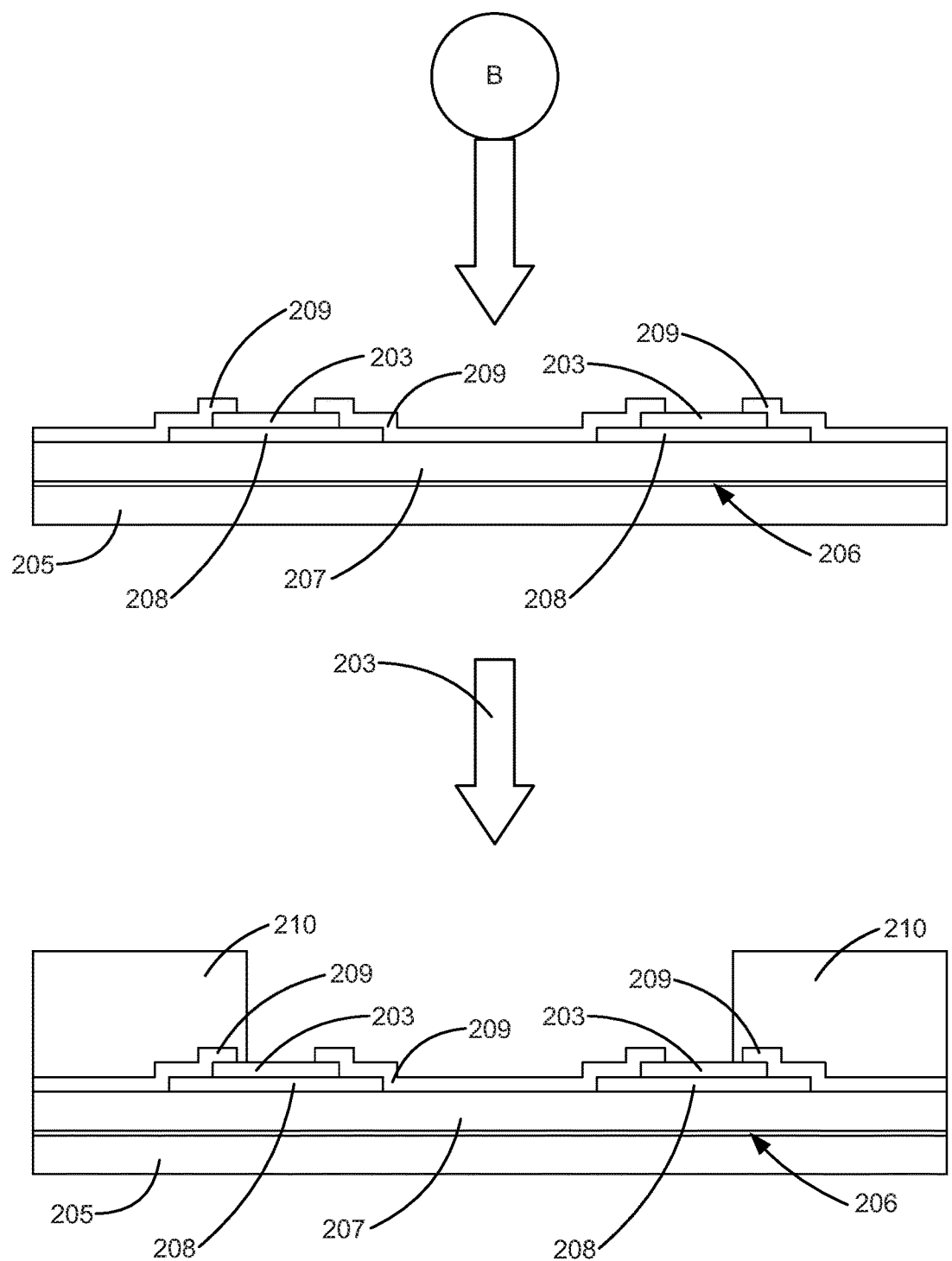

FIG. 2 is a side cut view of a microfluidic diagnostic chip (200) according to one example of the principles described herein. FIGS. 3A through 3C is a sequence of block diagrams showing a formation process of the microfluidic diagnostic chip of FIG. 2 according to an example of the principles described herein. As described above, the microfluidic diagnostic chip (200) includes at least one fluidic slot (201) into which an analyte may be introduced, a number of microfluidic channels (202) and a plurality of gold sensors (203). The number of microfluidic channels (202) may direct the analyte across a number of sensors such as plurality of gold sensors (203). In addition to the fluidic slot (201), microfluidic channels (202), and gold sensors (203), the microfluidic diagnostic chip (200) may further include a number of layers defining the fluidic slot (201) and microfluidic channels (202) and upon which the gold sensors (203) may be place.

The microfluidic diagnostic chip (200) may include a silicon substrate (204) through which the fluidic slot (201) is defined. The fluidic slot (201) may be formed such that a fluid including an analyte may be directed into a microfluidic channel (202). In an example, a first layer of dielectric material (205) may be deposited onto the silicon substrate (204). This first layer of dielectric material (205) may be layer of etchable dielectric material that is an oxide, oxynitride, or nitride of silicon, e.g., a tetraethylorthosilicate (TEOS) based oxide.

In an example, a passivation layer (206) may be placed on top of the first layer of dielectric material (205). In an example, the passivation layer (206) may be made of silicon carbide (SiC). In an example, the passivation layer (206) may have a thickness of 1000 Å. In an example, a second layer of dielectric material (207) may be placed over the passivation layer (206).

According to an example described herein, a layer of tantalum (208) may be deposited over a portion of the second layer of dielectric material (207). As described above the layer of tantalum may be 2000 Å thick.

On top of the layer of tantalum (208) a layer of gold forming the gold sensors (203) may be deposited on a portion of the tantalum (208). In this example, the layer of gold may further include number of bond pads and traces leading to the gold sensors (203) which are also made of gold. The thickness of the gold sensors (203) may be between 1500 Å to 3500 Å. The thickness of the gold bond pads and traces may be between 1500 Å to 3500 Å. In an example, the thickness of the gold sensors (203) is 2500 Å. In an example, the thickness of the gold bond pads and traces is 2500 Å. In one example, the layer of gold forming the gold sensors (203) may be subjected to a wet etching process. Wet etching is used in micro-fabrication to chemically remove layers from the surface of a substrate such as the layer of gold described herein. In a wet etch process, the surface to be etched can be submerged in a bath of acid or other reactive solution which chemically attacks areas that are unprotected by a photoresist layer or other non-reactive layer. Additionally, the wet etch bath may be tailored to preferentially attack specific materials such as the gold described herein. In an example, the layer of gold may be subjected to the wet etching process for about 30 seconds. During this process, the number of bond pads and traces leading to the gold sensors (203) being formed may be developed during the wet etching process. In addition to subjecting the gold layer to a wet etching process, other layers such as the silicon substrate (204), the dielectric material (205), the passivation layer (206), and the tantalum layer (208) may be subjected to a wet etching process.

In an example, on top of the tantalum layer (208) and layer of gold forming the gold sensors (203), a layer of silicon carbide (SiC) (209) is deposited. The layer of silicon carbide (209) may act as a die surface optimization material that chemically, electrically, and mechanically protects components of the microfluidic diagnostic chip (200).

In an example, the deposition of the layer of silicon carbide (SiC) (209) may be selective such that the entirety of the layer of gold forming the gold sensors (203) is not covered completely. In an example, the deposition of the layer of silicon carbide (SiC) (209) is accomplished by completely layering all surfaces and removing portions of the silicon carbide by, for example, dry etching. In this example, any electric fields produced by the gold sensors (203) may be precisely confined to a predetermined location within the microfluidic channels (202) without interference from an electric field produced by the tantalum layer (208). In an example, any exposed edges of the tantalum layer (208) may be covered entirely by the layer of silicon carbide (SiC) (209) so as to prevent any electric field produced by the tantalum from affecting the electric field generated by the gold sensors (203). Said differently, all exposed portions of the tantalum layer (208) are covered by the layer of silicon carbide (209). In an example, instead of depositing a silicon carbide layer (209), a combined layer of silicon nitride (SiN) and silicon carbide may be deposited.

A layer of epoxy material (210) may also be added over all of the above described layers. In an example, the layer of epoxy material (210) may be an epoxy-based negative photoresist that, when exposed to ultraviolet light, becomes cross-linked and hardened. As such this layer of epoxy material (210) may be formed into include a cavity (211) having a resistor (212) therein. The layer of epoxy material (210) may also have an orifice (213) defined therein. Here, as described above, the resistor (212) may heat up as a voltage is applied to it. The fluid including the analyte within the cavity (211) may be heated and ejected out of the microfluidic diagnostic chip (200) via the orifice (213).

A fluidic path (214) may be defined by the various layers described above. The fluid, including the analyte, may enter the microfluidic diagnostic chip (200) via the fluidic slot (201). As the analyte within the fluid is passed through the fluid path (214) it is analyzed and a determination may be made as to certain characteristics of the analyte leading, for example, to a potential diagnosis of a patient.

As briefly described above, the microfluidic diagnostic chip (100) may further include a number of other devices such as microfluidic pumps and a number of ejection resistors to push the fluid and analyte through the microfluidic channels (102) and eject the fluid and analyte out of the microfluidic diagnostic chip (100) via the orifice (213), respectively. The microfluidic pump may include a number of resistors that cause the fluid and analyte to heat up thereby driving the fluid and analyte through the number of microfluidic channels (102). The ejection resistors may heat the fluid and analyte sufficiently to create a cavitation bubble behind a bore defined in the microfluidic diagnostic chip (100). The created cavitation bubble may force the fluid and analyte out of the microfluidic diagnostic chip (100) and into, for example, a reservoir.

In an example, the microfluidic diagnostic chip (200) may include two types of resistors: a heater resistor and/or a pump resistor. Either kind of resistor may be placed within any portion of the microfluidic channels (202). In one example, a single resistor (212) may serve as both a pump and a heater based on the voltage applied to the resistor (212). In some examples, a resistor (212) acts as a heater when a voltage applied to it is below a threshold. This results in the fluid comprising the analyte that is in intimate contact with the resistor (212) not being nucleated. In one example, the voltage applied to the resistor (212) to function as a heater may be less than 5V. In an example, the voltage applied to the resistor meant to function as a heater may be greater than or less than 5V and may depend further on the properties of the fluid and temperature reached at the interface of the resistor (212) and fluid. In a heater resistor (212), the pulse time of the voltage application may vary based on the amount of heat to be created. Here, the longer the pulse and frequency at which the voltage is applied, the more heat is applied by the heater resistor (212) while the opposite is also true. In an example, the heater resistor (212) has a length of about 5 µm to about 1000 µm and a width of about 5 µm to about 1000 µm.

In some examples, the resistor (212) acts as a pump when a voltage applied to the resistor (212) is approximately 5V or higher. In these examples, the pulse time of the voltage application may be adjusted to vary the size of a drive bubble that is created when the heat from the pump resistor (212) is sufficient to vaporize fluid in intimate contact with the resistor (212).

The resistor (212) itself may be made of tantalum, platinum, gold, silicon carbide, silicon nitride, tungsten, or combinations thereof. In the case of a pump resistor (212), a rapid Joule heating method $$\left(\left(\frac{V^2 t}{R}\right)\right);$$

where V is the voltage, R is the resistance and t is the time) is used to superheat the fluid to create the drive bubble which grows and collapses in less than 10 µs. The rapid bubble creation and collapse causes net flow of fluid within the microfluidic channel (202). In one example, the pump resistor (212) has a length of about 5-110 µm and a width of about 5-100 µm. In another example, the pump resistor (212) is about 25 µm wide and about 25 µm long.

Figure 4:
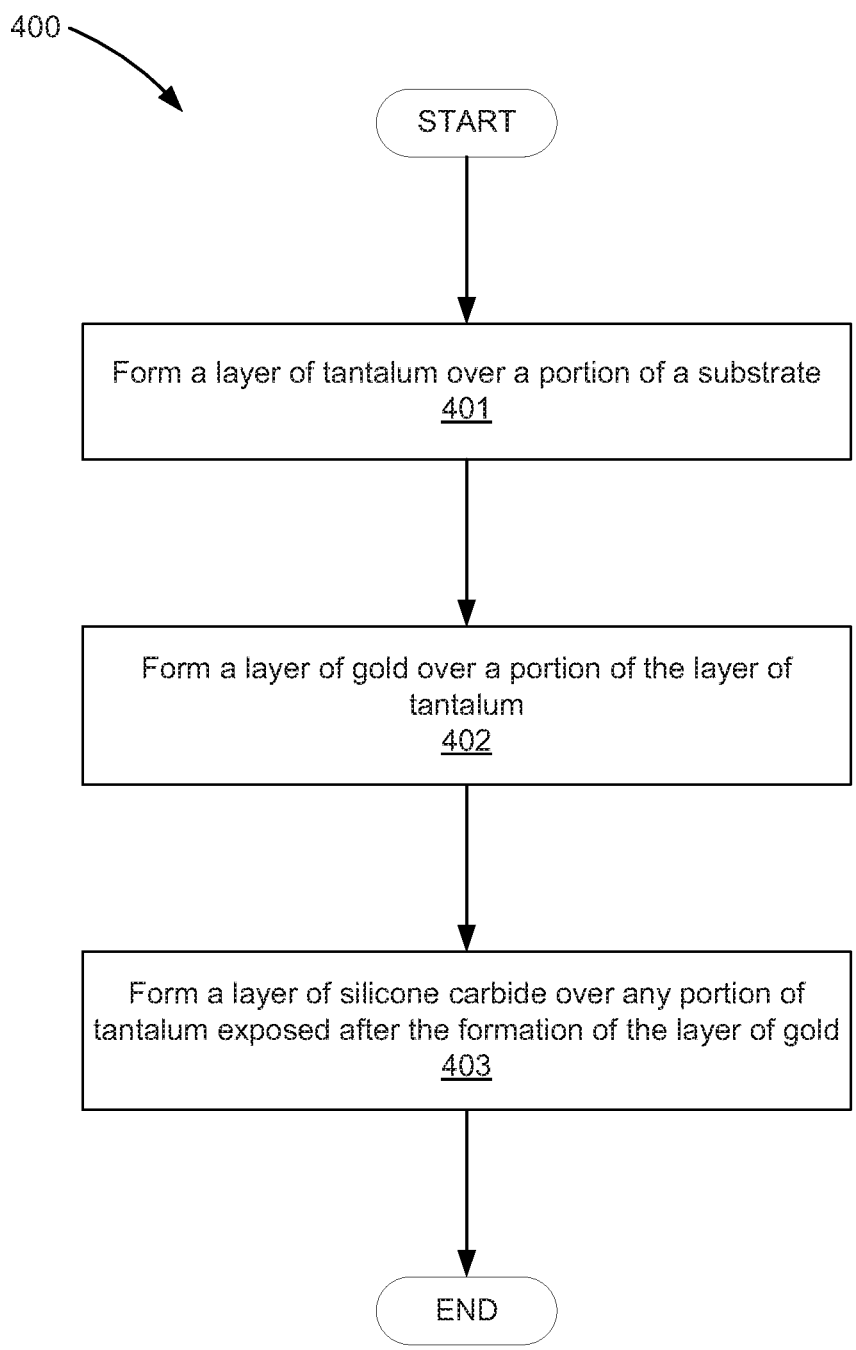
FIG. 4 is a flowchart showing method of forming a microfluidic diagnostic chip according to one example of the principles described herein.

FIG. 4 is a flowchart showing method (400) of forming a microfluidic diagnostic chip according to one example of the principles described herein. The method (400) may begin with forming (401) a layer of tantalum over a portion of a substrate. As described above, the tantalum may be formed over a dielectric material (205, 207). The tantalum layer (208) may be deposited over a portion of the dielectric material (205, 207).

The method (400) may continue with forming (402) layer of gold over a portion of the layer of tantalum (208) to form a number of gold sensors. In an example, the layer of gold may be deposited over a portion of the tantalum layer (208) as depicted in FIGS. 2 though 3C. The formation of the gold sensors may be accomplished by wet etching the layer of gold formed (402) over the tantalum (208).

The method (400) may further include forming (403) a layer of silicon carbide (SiC) (209) over any portion of tantalum exposed after the formation of the layer of gold. As described above, covering the tantalum layer (208) prevents or reduces interferences from an electric field created by the tantalum layer (208) as an electric charge is passed there through to the layer of gold forming the plurality of gold sensors (203). As a result, the electric field formed by passing an electric charge through the gold sensors (203) may more easily detect analytes in the fluid introduced into the microfluidic diagnostic chip (200).

Figure 5:
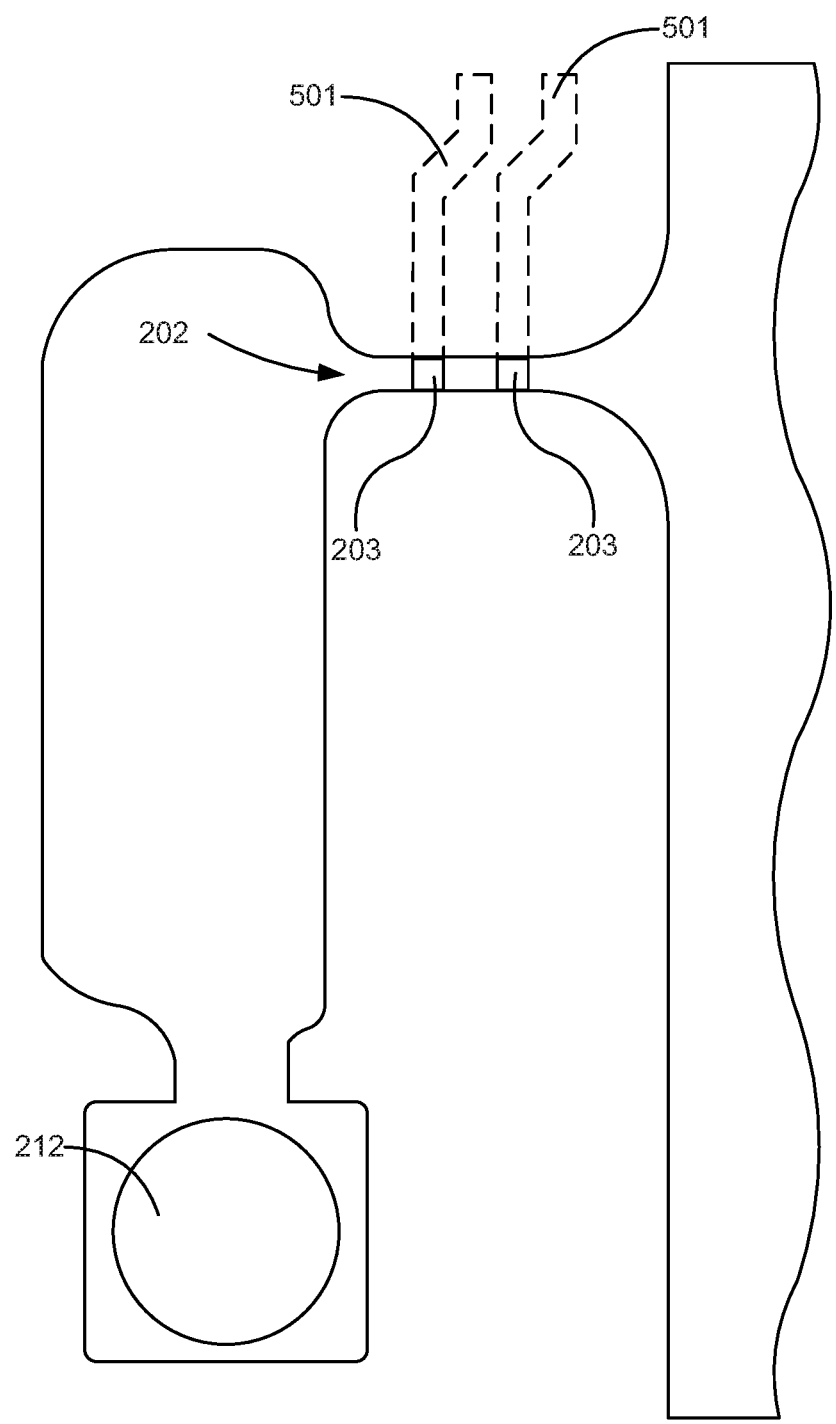
FIGS. 5-7 are a number of plan views showing a number of examples of gold sensors within microfluidic channels in a microfluidic diagnostic chip according to a number of examples of the principles described herein.
Figure 6:
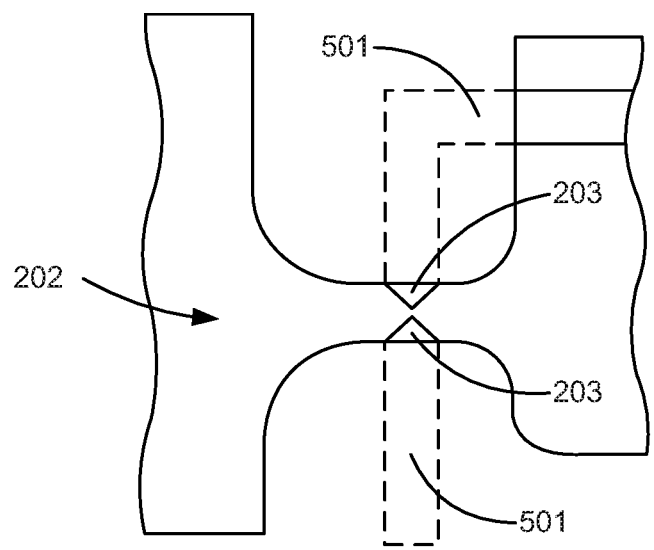
Figure 7:
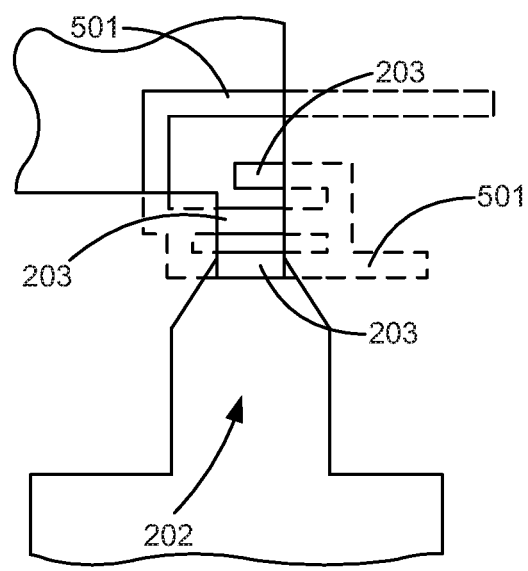

FIGS. 5-7 are a number of plan views showing a number of examples of gold sensors (203) within microfluidic channels (202) in a microfluidic diagnostic chip (200) according to a number of examples of the principles described herein. FIG. 5 shows a microfluidic channel (202), a number of gold sensors (203), and a resistor (212) as described above. In this example, the number of gold sensors (203) is two with the two gold sensors (203) acting as an electrode and ground respectively. FIG. 6 shows two triangular shaped gold sensors (203) within a microfluidic channel (202). The size, number, and shape of each of the gold sensors (203) may vary depending, in an example, on the type of analyte within the fluid being analyzed and the type of analysis being done among other factors. In a further example, FIG. 7 shows an arrangement of three gold sensors (203) within a microfluidic channel (202).

The MEMS devices included within the microfluidic diagnostic chip (100) described herein may be placed in a cassette that includes a number of electrical connections to the various gold sensors (203), pumps and resistors. The electrical connections of the cassette may be electrically coupleable to a computing device that provides relatively low levels of energy to the gold sensors (203), pumps and resistors in order to drive them. Additionally, the electrical connections of the cassette may receive signals from the gold sensors (203) indicative of characteristics of the analyte in the fluid. Based on the signals from the gold sensors (203) the computing device can provide to a user via, for example, a user interface, a data describing what the gold sensors (203) are detecting. Via this information a user can be provided with a diagnosis of an illness or provided with information regarding his or her health.

Aspects of the present system and method are described herein with reference to flowchart illustrations and/or block diagrams of methods, apparatus (systems) and computer program products according to examples of the principles described herein. Each block of the flowchart illustrations and block diagrams, and combinations of blocks in the flowchart illustrations and block diagrams, may be implemented by computer usable program code. The computer usable program code may be provided to a processor of a general purpose computer, special purpose computer, or other programmable data processing apparatus to produce a machine, such that the computer usable program code, when executed via, for example, a processor of the computing device or other programmable data processing apparatus, implement the functions or acts specified in the flowchart and/or block diagram block or blocks. In one example, the computer usable program code may be embodied within a computer readable storage medium; the computer readable storage medium being part of the computer program product. In one example, the computer readable storage medium is a non-transitory computer readable medium.

The specification and figures describe a gold sensor within a microfluidic diagnostic chip that creates an electric field in the presence of a fluid comprising an analyte. The thickness of the gold sensor being between 1500 and 5000 Å allows the electric field to be confined to a predetermined location within the microfluidic channels without interference being produced by rough edges of the gold sensor. Additionally, a passivation layer of silicon carbide may cover an underlying layer of tantalum on which the gold sensors are formed. This may protect the electric field created by the gold sensors from an electric field produced by the tantalum layer thereby preventing interference to the gold sensor's electric field. The relatively small thickness of the tantalum layer of approximately 2000 Å further reduces the electric field produced by the tantalum causing even more precise of an electric field produced by the gold sensors.

The preceding description has been presented to illustrate and describe examples of the principles described. This description is not intended to be exhaustive or to limit these principles to any precise form disclosed. Many modifications and variations are possible in light of the above teaching.

What is claimed is:

1. A microfluidic diagnostic chip, comprising:
   a number of microfluidic channels defined in a substrate, each microfluidic channel fluidly coupled to at least one fluidic slot, the at least one fluidic slot to receive a number of fluids;
   a number of gold sensors, each gold sensor having a thickness of between 1500 and 5000 angstroms (Å), a first fluidic feed slot into which an amount of an analyte is to be introduced fluidly coupled to a first of the fluidic channels;
   the number of gold sensors formed on top of a layer of tantalum; and
   a passivation layer formed over the tantalum, wherein the passivation layer does not cover the gold sensors;
   wherein the thickness of the passivation layer is 1500 Å.

2. The microfluidic diagnostic chip of claim 1, further comprising a resistor located at an outlet of the first of the microfluidic channels opposite the first fluidic feed slot corresponding to the first microfluidic channel, the resistor to pump fluid out the outlet of the first microfluidic channel to draw fluid across the gold sensors from the first fluidic feed slot corresponding to the first microfluidic channel.

3. The microfluidic diagnostic chip of claim 1, wherein the number of gold sensors comprises two triangular gold sensors.

4. The microfluidic diagnostic chip of claim 1, wherein the number of gold sensors comprises three gold sensors arranged in series along a first of the microfluidic channels.

5. The microfluidic diagnostic chip of claim 1, wherein the passivation layer comprises a mixture of silicon nitride and silicon carbide.

6. A microfluidic diagnostic chip, comprising:
   a number of microfluidic channels defined in a substrate, each microfluidic channel fluidly coupled to at least one fluidic slot; the at least one fluidic slot to receive a number of fluids:
   a number of gold sensors, each gold sensor having a thickness of between 1500 and 5000 angstroms (Å);
   a layer of tantalum intermediate to the substrate and the gold sensors;
   a layer of silicon carbide, the layer of silicon carbide covers exposed portions of the layer of tantalum to prevent interference in an electric field created by the gold sensors as the gold sensors receive a charge;
   wherein the thickness of the silicon carbide is 1500 Å.

7. The microfluidic diagnostic chip of claim 6, wherein an exposed surface of each of the gold sensors acts as a binding surface to be functionalized by binding thereto an antibody.

8. The microfluidic diagnostic chip of claim 6, wherein the layer of tantalum has a thickness of 2000 Å.

9. The microfluidic diagnostic chip of claim 6, further comprising a resistor located at an outlet of a first of the microfluidic channels opposite the fluidic slot corresponding to the first microfluidic channel, the resistor to pump fluid out the outlet of the first microfluidic channel to draw fluid across the gold sensors from the fluidic slot corresponding to the first microfluidic channel.

* * * * *